July 13, 1937. F. H. HOWARD Plant Pat. 256
ROSE
Filed Dec. 21, 1936
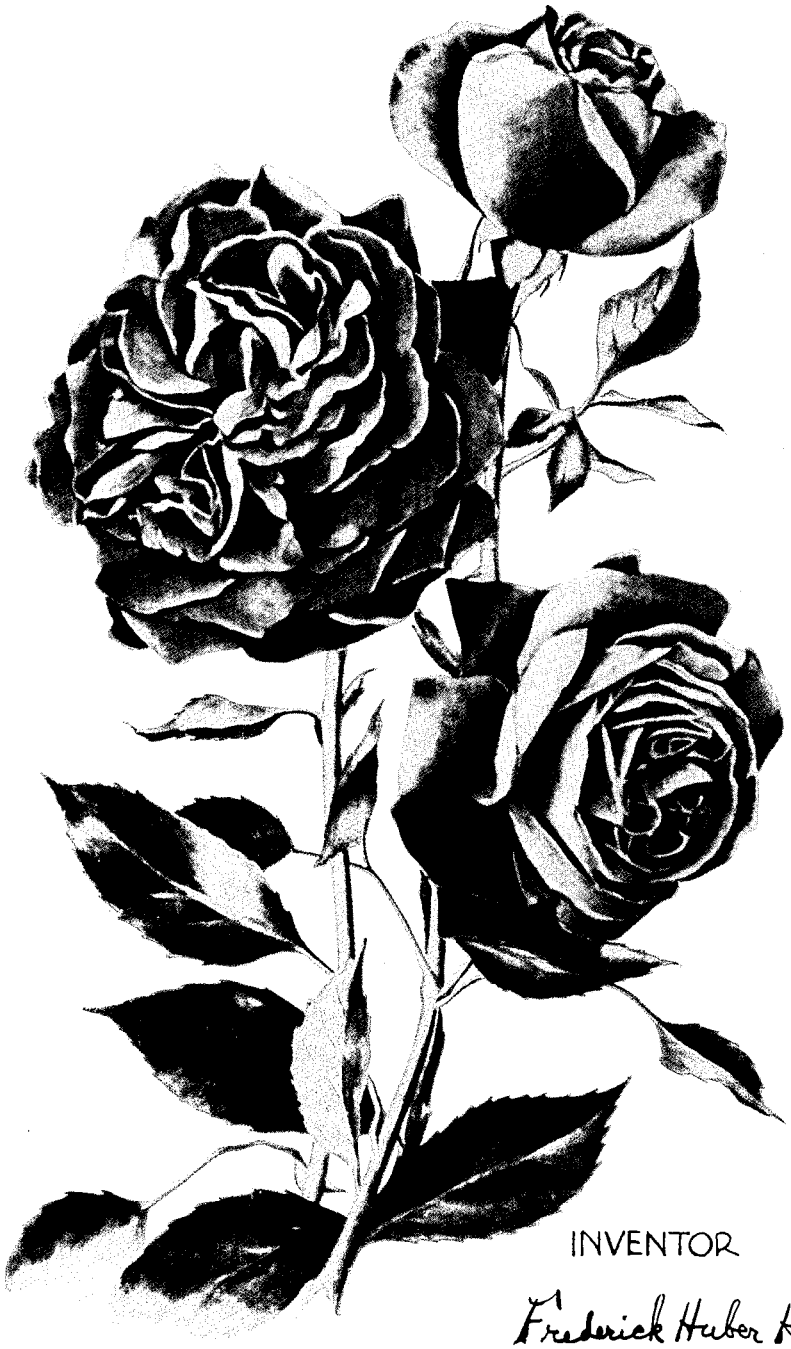
INVENTOR
Frederick Huber Howard
By Orville M. Kile
PLANT PATENT AGENT Patented July 13, 1937

Plant Pat. 256

UNITED STATES PATENT OFFICE

256

ROSE

Frederick Huber Howard, Montebello, Calif.

Application December 21, 1936, Serial No. 117,086

1 Claim. (Cl. 47—61)

This new variety of rose is a hybrid from a line of unnamed seedlings and is the result of much cross breeding in an effort to produce a fragrant, dark velvety red rose that would not "blue."

The accompanying illustrations show in full color and with approximate accuracy three specimens of this variety in various stages of opening, together with leaves and stems. It must be understood, however, that the artist cannot truly show the velvety sheen.

This successful cross was produced in 1933 and several subsequent asexually-produced generations have shown the qualities to be permanent.

Following is a more detailed description of this new variety.

*The plant*

*Growth habits.*—Very vigorous bush form; perpetual and free bloomer.

*Stems.*—Stiff; strong; bright green; very thorny.

*Nodes.*—Short and inclined to stagger.

*Peduncle.*—Usually about 3 inches in length; smooth; bright green, slightly lighter than stem.

*Foliage.*—Abundant but rather small.

*Leaves.*—Compound, consisting of from 3 to 5 leaflets. Soft but leathery.

*Leaflets.*—Narrowly oval with acute apex. Terminal leaflet is usually about twice as large as lateral ones in same group. Terminal leaflets average 2½ inches in length by about 1½ inches in width. Margin sharply serrated.

*Color.*—Upper surface is Varley's Green (Ridgway's Color Standards and Nomenclature, Plate XVIII). Under surface is much lighter green, with frequent reddish splotches.

*Rachis.*—Grooved and smooth on upper surface; under side frequently with fine spines.

*Stipules.*—Moderately long and wide with long sharp points.

*Sepals.*—Moderate length.

*The flower*

Bud:

*Form.*—Globular.

*Color.*—Approaches Oxblood Red (Plate I).

*Opening.*—Opens rather slowly but evenly.

Bloom:

*Form.*—Imbricated. This form is retained, the stamens and pistils remaining hidden until the flower dies.

*Size.*—Three and one-half to four inches across when fully opened.

*Petalage.*—Very double, 50 petals in month of October in inventor's garden. Petals arranged regularly around outer edges but inner petals folded and compressed.

*Petals.*—Soft and rather thick. Inside velvety.

*Behavior.*—Cling tenaceously until flower dies.

*Shape.*—Obovate, with inner petals narrower and more pointed than outer ones.

*Color.*—Upper side of petal is deep red with velvety sheen. Under side of petal is somewhat lighter and without sheen. Each petal has a small white area at point of attachment but no white is visible when observing the open rose.

*General color effect.*—This rose is popularly described as being sable crimson. There is no color in Ridgway's which describes it although the color lies between Carmine and Oxblood Red (Plate I) with a slight touch of Bordeaux (Plate XII). This rose retains its vivid coloring without becoming "blued."

*Keeping qualities.*—Good; cut flowers lasting 4 or 5 days in good condition in ordinary room temperatures.

*Fragrance.*—Extremely fragrant (more fragrant than any other red rose known to me).

*Reproductive organs*

*Stamens.*—Many; uneven; arranged around pistils.

*Filaments.*—Varying lengths; reddish.

*Anthers.*—Medium; brown.

*Pollen.*—Scarce.

*Pistils.*—Very many; bunched.

*Styles.*—Uneven; white; hairy.

*Stigma.*—Reddish brown with white tips.

*Ovaries.*—Enclosed in calyx.

*Hips.*—Small; smooth; green.

Having disclosed my invention, I claim;

The new and distinct variety of rose plant herein illustrated and described, characterized particularly by its vigorous growth and lavish production of deep red blossoms which retain their color without bluing; and by its intense fragrance unusual in red roses.

FREDERICK HUBER HOWARD.